United States Patent
Gyory

[19]
[11] Patent Number: 5,562,607
[45] Date of Patent: Oct. 8, 1996

[54] ELECTROTRANSPORT DEVICE HAVING REUSABLE CONTROLLER POWER SAVER

[75] Inventor: J. R. Gyory, San Jose, Calif.

[73] Assignee: ALZA Corporation, Palo Alto, Calif.

[21] Appl. No.: 374,940

[22] Filed: Jan. 18, 1995

[51] Int. Cl.⁶ ........................................... A61N 1/30
[52] U.S. Cl. ............................. 604/20; 439/188; 439/909
[58] Field of Search ...................... 604/20–21; 200/51 R; 607/149–153, 115; 439/188, 909

[56] References Cited

U.S. PATENT DOCUMENTS

| | | | |
|---|---|---|---|
| 4,141,359 | 2/1979 | Jacobsen et al. | 128/172.1 |
| 4,474,570 | 10/1984 | Ariura et al. | 604/20 |
| 4,808,152 | 2/1989 | Sibalis | 604/20 |
| 5,006,108 | 4/1991 | LaPrade | 604/20 |
| 5,047,007 | 9/1991 | McNichols et al. | 604/20 |
| 5,135,479 | 8/1992 | Sibalis et al. | 604/20 |
| 5,167,617 | 12/1992 | Sibalis | 604/20 |
| 5,224,927 | 7/1993 | Tapper | 604/20 |
| 5,224,928 | 7/1993 | Sibalis et al. | 604/20 |
| 5,246,418 | 9/1993 | Haynes et al. | 604/20 |
| 5,254,081 | 10/1993 | Maurer et al. | 604/20 |
| 5,320,597 | 6/1994 | Sage, Jr. et al. | 604/20 |
| 5,358,483 | 10/1994 | Sibalis | 604/20 |

FOREIGN PATENT DOCUMENTS

| | | | |
|---|---|---|---|
| 1267046 | 3/1972 | United Kingdom | 607/9 |
| 2239803 | 7/1991 | United Kingdom . | |

*Primary Examiner*—Randall L. Green
*Assistant Examiner*—Mark Bockelman
*Attorney, Agent, or Firm*—D. Byron Miller; Steven F. Stone; Edward L. Mandell

[57] ABSTRACT

An electrotransport system (50) includes a reusable controller (52) having a power source (60) and a separable disposable drug-containing unit (70). The controller (52) contains a switch (62) which disconnects the power source (60) from current drain when the controller (52) is uncoupled from the drug unit (70). A coupling means (74,66,105,72,64,104) physically and electrically connects together the controller (52) and the drug unit (70) such that the controller (52) provides electrical current to the drug unit (70) for electrotransport delivery of the drug to a body surface (eg, the skin) of a patient.

20 Claims, 8 Drawing Sheets

5,562,607

ELECTROTRANSPORT DEVICE HAVING REUSABLE CONTROLLER POWER SAVER

TECHNICAL FIELD

The invention relates to electrotransport drug delivery systems having a drug containing delivery unit and a reusable control unit having an electrically powered control circuit, the units separably connected by a mechanical coupler.

BACKGROUND ART

The term "electrotransport" as used herein refers generally to the delivery of an agent (eg, a drug) through a membrane, such as skin, mucous membrane, or nails. The delivery is induced or aided by application of an electrical potential. For example, a beneficial therapeutic agent may be introduced into the systemic circulation of a human body by electrotransport delivery through the skin. A widely used electrotransport process, electromigration (also called iontophoresis), involves the electrically induced transport of charged ions. Another type of electrotransport, electroosmosis, involves the flow of a liquid, which liquid contains the agent to be delivered, under the influence of an electric field. Still another type of electrotransport process, electroporation, involves the formation of transiently-existing pores in a biological membrane by the application of an electric field. An agent can be delivered through the pores either passively (ie, without electrical assistance) or actively (ie, under the influence of an electric potential). However, in any given electrotransport process, more than one of these processes may be occurring simultaneously to a certain extent. Accordingly, the term "electrotransport", as used herein, should be given its broadest possible interpretation so that it includes the electrically induced or enhanced transport of at least one agent, which may be charged, uncharged, or a mixture thereof, whatever the specific mechanism or mechanisms by which the agent actually is transported.

Electrotransport devices use at least two electrodes that are in electrical contact with some portion of the skin, nails, mucous membrane, or other surface of the body. One electrode, commonly called the "donor" or "active" electrode, is the electrode from which the agent is delivered into the body. The other electrode, typically termed the "counter" or "return" electrode, serves to close the electrical circuit through the body. For example, if the agent to be delivered is positively charged, ie, a cation, then the anode is the active or donor electrode, while the cathode serves to complete the circuit. Alternatively, if an agent is negatively charged, ie, an anion, the cathode is the donor electrode. Additionally, both the anode and cathode may be considered donor electrodes if both anionic and cationic agent ions, or if uncharged or neutrally charged agents, are to be delivered.

Furthermore, electrotransport delivery systems generally require at least one reservoir or source of the agent to be delivered, which is typically in the form of a liquid solution or suspension. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically, one pole of the power source is electrically connected to the donor electrode, while the opposite pole is electrically connected to the counter electrode. In addition, some electrotransport devices have an electrical controller that controls the current applied through the electrodes, thereby regulating the rate of agent delivery. Furthermore, passive flux control membranes, adhesives for maintaining device contact with a body surface, insulating members, and impermeable backing members are other optional components of an electrotransport device.

All electrotransport agent delivery devices utilize an electrical circuit to electrically connect the power source (eg, a battery) and the electrodes. In very simple devices, such as those disclosed in Ariura et al U.S. Pat. No. 4,474,570, the "circuit" is merely an electrically conductive wire used to connect the battery to an electrode. Other devices use a variety of electrical components to control the amplitude, polarity, timing, waveform shape, etc of the electric current supplied by the power source. See, for example, McNichols et al U.S. Pat. No. 5,047,007.

To date, commercial transdermal electrotransport drug delivery devices (eg, the Phoresor, sold by Iomed, Inc. of Salt Lake City, Utah; the Dupel Iontophoresis System sold by Empi, Inc. of St. Paul, Minn.; the Webster Sweat Inducer, model 3600, sold by Wescor, Inc. of Logan, Utah) have generally utilized a desk-top electrical power supply unit and a pair of skin contacting electrodes. The donor electrode contains a drug solution while the counter electrode contains a solution of a bio-compatible electrolyte salt. The "satellite" electrodes are connected to the electrical power supply unit by long (eg, 1–2 meters) electrically conductive wires or cables. Examples of desk-top electrical power supply units which use "satellite" electrode assemblies are disclosed in Jacobsen et al U.S. Pat. No. 4,141,359 (see FIGS. 3 and 4); LaPrade U.S. Pat. No. 5,006,108 (see FIG. 9); and Maurer et al U.S. Pat. No. 5,254,081 (see FIGS. 1 and 2). The power supply units in such devices have electrical controls for adjusting the amount of electrical current applied through the electrodes. The "satellite" electrodes are connected to the electrical power supply unit by long (eg, 1–2 meters) electrically conductive wires or cables. Wire connections are subject to disconnection, limit patient movement and mobility and can also be uncomfortable. The wires connecting the power supply unit to the electrodes limits their separation to the length of the wires provided.

More recently, small self-contained electrotransport delivery devices adapted to be worn on the skin, sometimes unobtrusively under clothing, for extended periods of time have been proposed. The electrical components in such miniaturized electrotransport drug delivery devices are also preferably miniaturized, and may be either integrated circuits (ie, microchips) or small printed circuits. Electronic components, such as batteries, resistors, pulse generators, capacitors, etc, are electrically connected to form an electronic circuit that controls the amplitude, polarity, timing, waveform shape, etc of the electric current supplied by the power source. Such small self-contained electrotransport delivery devices are disclosed for example in Tapper U.S. Pat. No. 5,224,927; Sibalis et al U.S. Pat. No. 5,224,928 and Haynes et al U.S. Pat. No. 5,246,418. Unfortunately, as electrotransport delivery devices become smaller, the power source (eg, batteries) used to power the devices, must also become smaller and hence, battery capacity and battery life become more of a design problem.

In addition to electrotransport devices becoming smaller, there have recently been suggestions to utilize electrotransport devices having a reusable controller which is adapted to be used with multiple drug-containing units. The drug-containing units are simply disconnected from the controller when the drug becomes depleted and a fresh drug-containing unit is thereafter connected to the controller. In this way, the relatively more expensive hardware components of the device (eg, batteries, LED's, circuit hardware, etc) can be contained within the reusable controller, and the relatively less expensive donor reservoir and counter reservoir matrices can be contained in the disposable drug containing unit thereby bringing down the overall cost of electrotransport drug delivery. Examples of electrotransport devices comprised of a reusable controller adapted to be removably connected to a drug-containing unit are disclosed in Sage, Jr. et al, U.S. Pat. No. 5,320,597; Sibalis, U.S. Pat. No. 5,358,483; Sibalis et al, U.S. Pat. No. 5,135,479 (FIG. 12); and Devane et al UK Patent Application 2, 239 803.

DESCRIPTION OF THE INVENTION

It is an aspect of the present invention to provide an electrotransport system in which the power source in the reusable control unit is electrically disconnected from the current controlling circuit, which circuit includes a closed internal circuit path, until the time when the unit is ready to be used.

The present invention is directed to preserving battery strength and extending battery life in an electrotransport device comprised of a reusable electronic controller adapted to be used with a plurality of single use (eg, disposable) drug-containing units. After the drug has been depleted from the drug-containing unit, the unit is disconnected from the controller and discarded, and then replaced with a fresh one. The controller includes a power source (eg, one or more batteries) and a circuit for controlling the timing, frequency, magnitude, etc of the current applied by the device. The control circuit includes an internal circuit, such as a timing circuit, which at the time the device is in operation, is in contact with both poles of the battery through a circuit path other than the patient's body. A switch is provided for keeping the batteries electrically isolated from the closed internal circuit until the time when the device is placed in operation. The switch is closed automatically by coupling the disposable drug-containing unit to the reusable electronic controller. The switch is automatically reopened, and the battery(ies) again put in electrical isolation, when the drug-containing unit is uncoupled from the reusable controller.

The invention is useful in any electrotransport device comprised of a reusable controller and single use/disposable drug units, particularly for preventing current drain during shelf life between the time when the device is manufactured and the time it is first used on a patient. The invention is particularly useful in electrotransport devices having long periods of non-use (eg, over night, on holidays/weekends, etc) once the controller is unpackaged and put into use.

BRIEF DESCRIPTION OF THE DRAWINGS

In the figures, wherein like parts are given like reference numerals and wherein.

MODES FOR CARRYING OUT THE INVENTION

Figure 1:
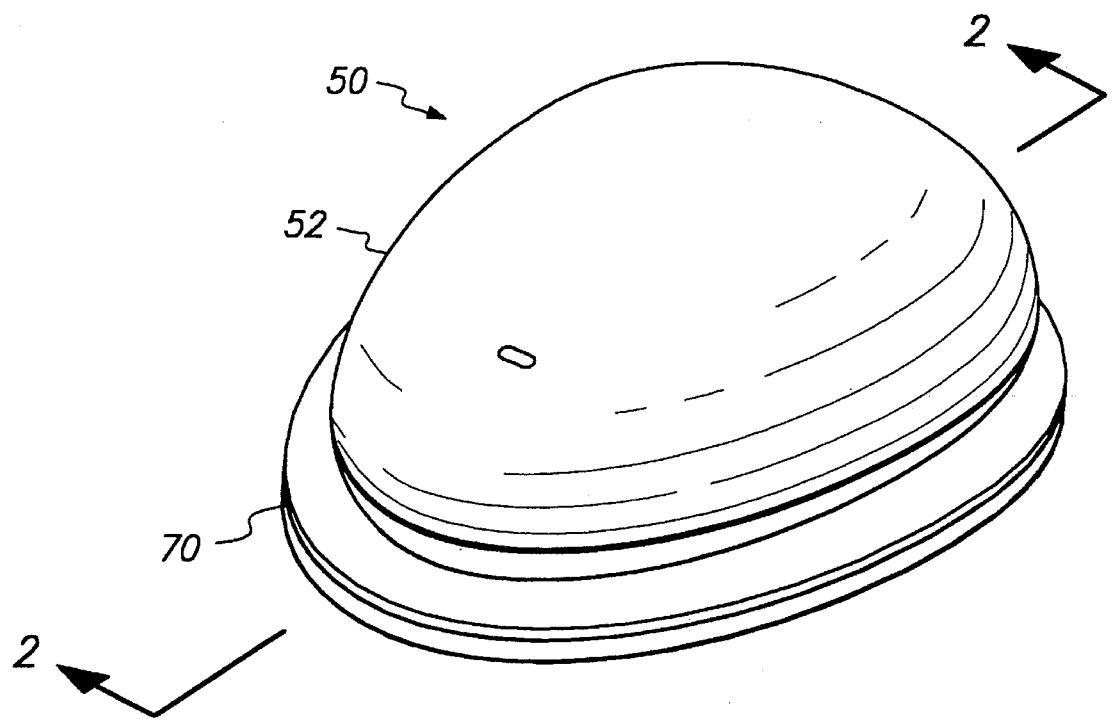
FIG. 1 is a perspective view of a separable electrotransport device in accordance with this invention.

FIG. 1 is a perspective view of electrotransport device 50 having a reusable electronic controller 52 which is adapted to be coupled to and uncoupled from, drug-containing unit 70. The controller 52 is reusable, ie, it is adapted to be used with a plurality of drug units 70, eg, a series of identical and/or similar drug units 70. On the other hand, drug unit 70 typically has a more limited life and is adapted to be discarded after use, ie, when the drug contained therein has been delivered or has been depleted.

Figure 2:
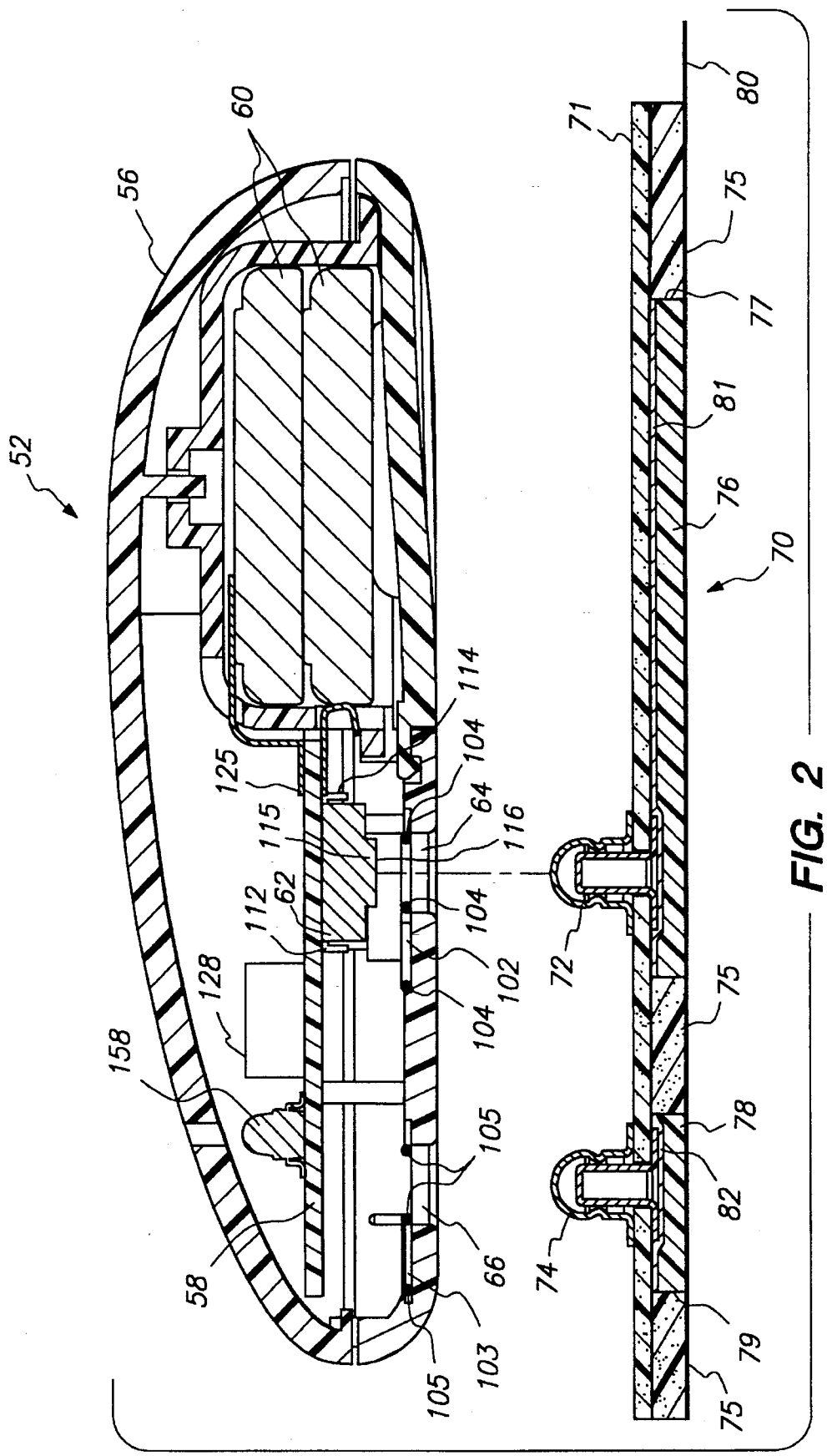
FIG. 2 is a cross sectional view of the device shown in FIG. 1, taken along line 2—2 of FIG. 1, showing the controller and the drug unit in an uncoupled configuration.

With reference to FIG. 2, there is shown a sectional view of the system 50 along line 2—2 of FIG. 1, with the drug unit 70 uncoupled from the controller 52. The housing 56 of controller 52 encloses a printed circuit (PC) board 58, a battery power source 60, comprised of two button cell batteries connected in series, for powering the PC board 58 and a switch 62 for connecting and disconnecting the power source 60 from the PC board 58. The PC board 58 is formed in a conventional manner, having conductive traces patterned for interconnecting components thereon.

The drug unit 70 is configured to be removably coupled to the controller 52, with the top of drug unit 70 adjacent to and facing the bottom of the controller 52. The top of assembly 70 is provided with the male parts of two snap type connectors, the male parts being studs 72 and 74 which extend upwardly from drug unit 70. The bottom portion of the housing 56 is provided with two openings 64 and 66 which are positioned and sized to receive studs 72 and 74, respectively.

The drug unit 70 includes a liquid impermeable, flexible insulating substrate 71 which is adhered or laminated to foam member 75 having wells 77 and 79 therein. The substrate 71 may be made of a polyethylene foam or polyester. The foam member 75 may be made of a layer of polyethylene foam of predetermined thickness having the wells 77 and 79 defined by punching or cutting as is well known in the art. The wells 77 and 79 each contain a reservoir and optionally an electrode 81, 82, respectively. Thus, well 77 contains reservoir 76 and optionally electrode 81, and well 79 contains reservoir 78 and optionally electrode 82. At least one of the reservoirs 76 and 78 (eg, reservoir 76) contains a therapeutic agent (eg, a drug) to be delivered. Thus, electrode 81 and reservoir 76 may be considered a donor electrode assembly while electrode 82 and reservoir 78 may be considered counter electrode assembly. The reservoirs 76 and 78 are typically formed from hydrogels and are adapted to be placed in contact with the body surface (eg, skin) of a patient (not shown) when in use.

The reservoirs 76 and 78 are enclosed around the periphery of the substrate 71 and isolated from each other by foam member 75. The bottom (ie, patient contacting) surface of foam member 75 is preferably coated with a skin contact adhesive. A release liner 80 covers the body contacting surfaces of the two reservoirs 76 and 78 and the adhesive coated surface of foam member 75 before the unit 70 is put in use. The release liner 80 is preferably a silicone coated polyester sheet. The release liner 80 is removed when the unit 70 is applied to the skin of a patient (not shown).

Studs 72 and 74 are made from an electrically conductive material (eg, a metal such as silver, brass, stainless steel, etc or a metal coated polymer, eg, ABS with a silver coating). Thus, both studs 72 and 74 conduct electric current supplied by controller 52. The stud 72 makes electrically conductive contact with the electrode 81 and the reservoir 76 while stud 74 makes electrically conductive contact with the electrode 82 and the reservoir 78.

Housing 56 of controller 52 has recesses 102 and 103 immediately inboard of openings 64 and 66, respectively. Spring retainers 104 and 105, which are electrically conductive and radially resilient, are configured to be received by the recesses 102, 102'. The spring retainers 104 and 105 are configured to removably latch in the respective circumferential grooves when the studs 72 and 74 are inserted through openings 64 and 66. The studs 72, 74 are demountably retained by the respective spring retainers 104, 105, thus removably connecting the drug unit 70 to the housing 56 of controller 52.

Conventional electronic connecting means (eg, conductive wires, traces or leaf springs (not shown) electrically connect the spring retainers 104, 105 to respective conductive traces (not shown) on the bottom of the PC board 58.

A single pole, single throw, switch 62, such as the type SKHUAB, or SKHUAA, available from the Alps Electric(USA), Inc, San Jose, Calif. is mounted to the bottom of the PC board 58. The switch 62 includes two terminals 112, 114 soldered or otherwise electrically connected to respective traces (not shown) on the PC board 58. One terminal 114 of the switch 62 is electrically connected to one pole of the battery power source 60 while the other pole of the battery power source 60 is electrically connected to system ground 125. The other switch terminal 112 is connected to an input terminal 126 of a current control circuit 128.

The switch 62 includes a spring biased plunger 115 having an actuating face 116 oriented roughly parallel to the bottom surface of controller 52. The switch 62 is disposed on the bottom of the PC board 56 such that the actuating face 116 and the opening 64 are aligned essentially coaxial to the stud 72 when stud 72 is inserted into opening 64. The plunger 115 is shown in its fully extended position in FIG. 2, ie when the drug unit 70 is uncoupled from controller 52. Plunger 115 retracts against the force of the internal spring when the stud 72 pushes against the actuating face 116 during the coupling of drug unit 70 to the controller 52.

Figure 3:
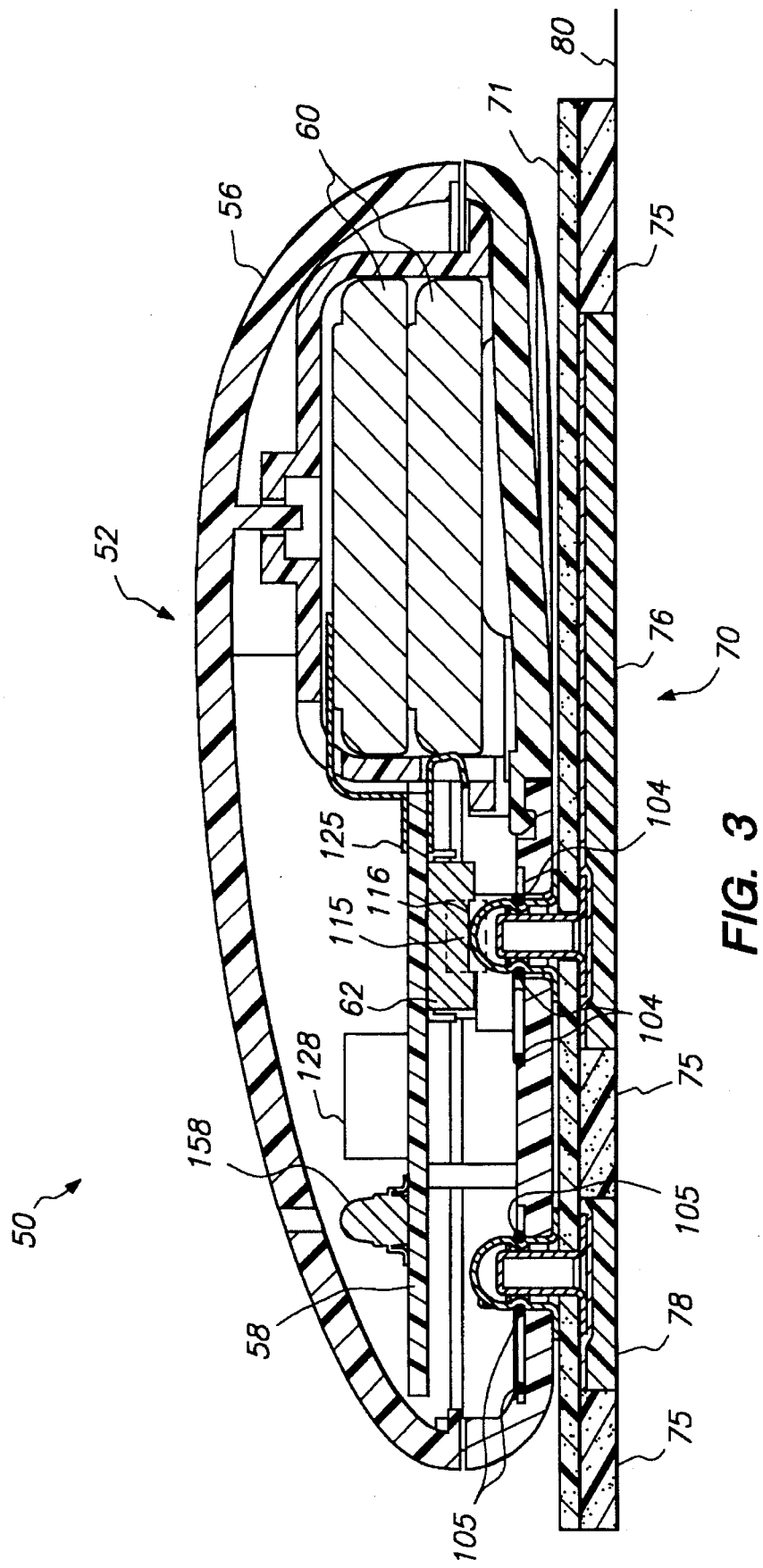
FIG. 3 is a cross sectional view of the device shown in FIG. 1, taken along line 2—2 of FIG. 1, showing the controller and the drug unit in a coupled configuration.

The switch terminals 112, 114 are open (ie, the switch 62 is open) when the drug unit 70 is uncoupled from the controller 52 and the spring in the plunger 115 is in an extended configuration. The switch terminals 112, 114 are electrically connected (ie, the switch 62 is closed) when the plunger 115 is in a retracted configuration, ie, when drug unit 70 is coupled to controller 52 as shown in FIG. 3.

The PC board 58 and the switch 62 are mounted within the housing 56 such that the stud 72 simultaneously causes (i) plunger 115 to retract and electrically connect the terminals 112, 114 of the switch 62, and (ii) mechanically couple the drug unit 70 to the controller 52, by means of the spring retainer 104.

Figure 4:
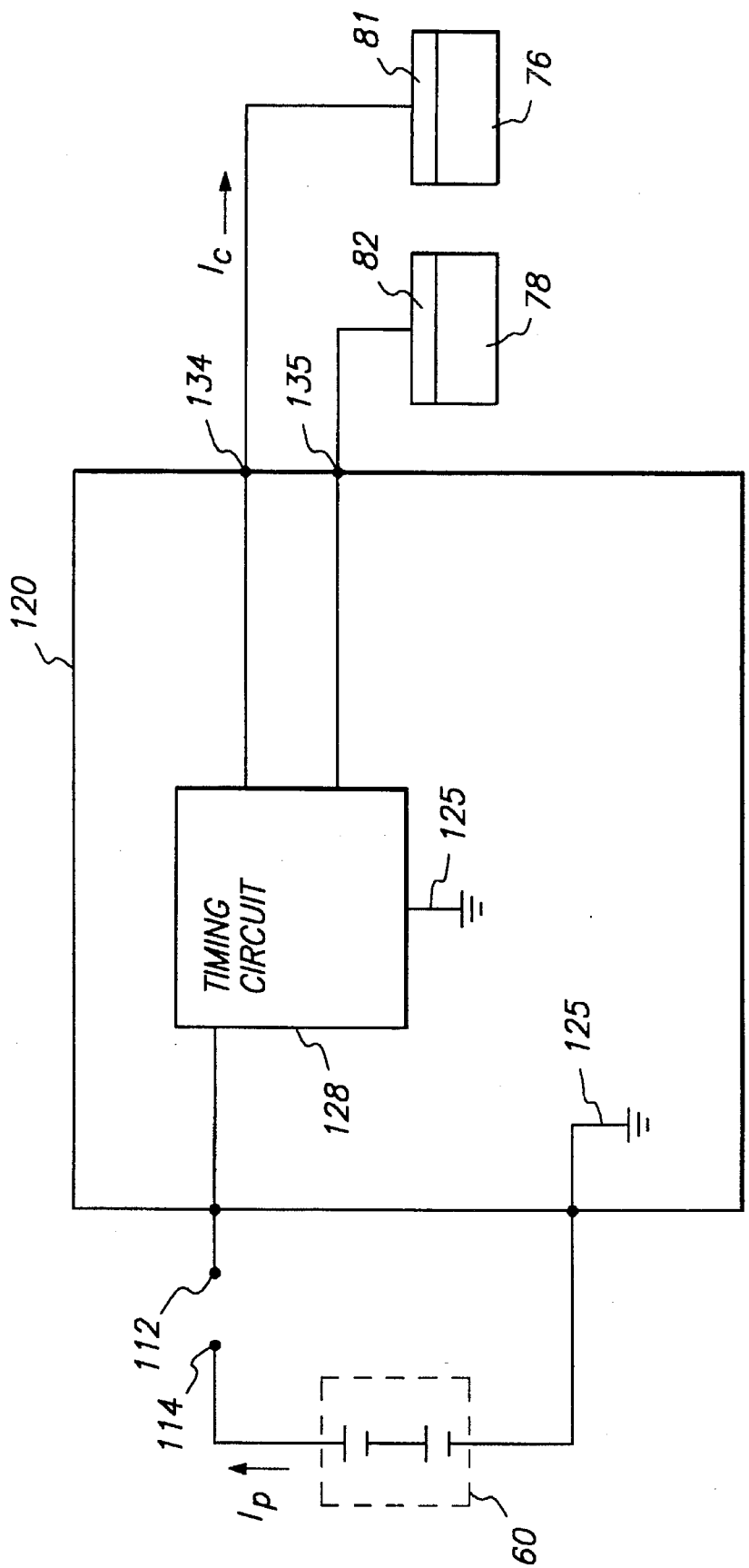
FIG. 4 is an electrical schematic drawing of a preferred embodiment of the present invention.

The switch terminals 112, 114 are electrically connected in series with a power supply circuit carried on PC board 58. While the present invention is not limited to any current level, circuitry, time or mode of drug delivery, one example of a timed power supply circuit (ie, applies electrotransport current to a patient for a predetermined period of time) is illustrated in FIG. 4.

The control circuit 120 includes two output terminals 134 and 135 for providing control current, Ic, to the electrode assemblies 81, 76 and 82, 78. The controlled current, Ic, is supplied to the skin of a patient when the electrode assembly 70 and controller housing 56 are mounted together as described above, and the reservoirs 76, 78 are affixed to the skin or mucous membranes of a patient. The power supply current, Ip, to the control circuit 128 is zero until the two switch terminals 112, 114 are connected by closure of the switch 62 (not shown in FIG. 4) upon actuation of the plunger 115. The timing circuit 128, therefore is constrained to draw no quiescent current from the power supply 60, and to supply zero current, Ic, until the switch 62 is closed by the mechanical coupling of the drug unit 70 to the controller 52. This ensures that the energy stored in the power source 60 will be conserved until the controller 52 and the drug unit 70 are coupled as described earlier.

The two outputs 134, 135 are connected through the conductive segments to the donor electrode assembly 81, 76 and counter electrode assembly 82, 78 respectively, through conductive traces (not shown) configured on the PC board 58, which make electrical contact with the corresponding one of the ends of the spring retainers 104, 105.

The current, Ic, for supplying the therapeutic agent contained in the reservoir 76, flows from the output 134, through the spring retainer 104, the stud 82, the electrode 81 and the reservoir 76 into the body of the patient (not shown).

Alternative embodiments of a control circuit 120 may use other controlled current waveforms than successive constant current values. Pulsed, sinusoidal, ramp and multiple combinations of such various time varying waveforms may also be supplied by the method of feedback control as desired.

In use, with reference again to FIG. 2–4, the patient, or clinical practitioner selects the reusable controller 52 and the desired disposable electrode assembly 70. The controller 52 and assembly 70 may have been stored in an inactive condition for an indefinite period of time without causing current drain from the battery power source 60 since the switch 62 is in a normally open condition.

The studs 72 and 74 are aligned with the respective openings 64 and 66 in the housing 56 and inserted therein. The studs are self-guided upon insertion to make conductive contact with the respective spring retainers 104 105. Continued insertion of the studs 72 and 74 causes the spring retainers 104, 105 to slide around the heads of the studs until the retainers 104, 105 engage with the grooves of the studs. Simultaneously, the head of stud 72 physically displaces the actuator plunger 115 which causes electrical connection between switch terminals 112, 114. The terminals 112, 114 thus complete the connection of the power source 60 in the circuit 120. The engagement of the retainers 104, 105 in the grooves of studs 72, 74 now complete the mechanical coupling of the housing 56 and the drug unit 70 to form a single unit. Optionally, the completed coupling of drug unit 70 to controller 52 may be signalled to the user by means of flashing the LED 158 with a predetermined blinking pattern after the switch 62 is closed. The coupled device 50 is then placed on the body of a patient with the reservoirs 76, 78 making contact with the patient body surface (eg, skin). When connection is made between the reservoirs 76, 78 and the patient's skin, the current, Ic, begins to flow through the electrode assemblies 81, 76 and 82, 78 and through the patient's body.

Delivery of controlled current, Ic, continues until completion of the timed program in timing circuit 128, exhaustion of the therapeutic agent in the reservoir 76 or removal of the system 50 from the patient's skin.

Completion of a predetermined time of therapeutic agent delivery or exhaustion of the disposable electrode assembly 70 may be indicated, for example, by flashing the LED 158.

The patient or clinical operator may then disengage the studs 72, 74 of exhausted drug unit 70 from the openings 64, 66 and retainer springs 104, 105 of the housing 56 by pulling the drug unit 70 away from the housing 56. The removal of the stud 72 from opening 64 allows the plunger 115 to extend once again thereby causing switch 62 to open and disconnect the power source 60 from the power circuit 120. Opening the power circuit 120 preserves the remaining battery charge on the power source 60. A replacement drug unit 70 may be mounted to the housing 56 and installed to actuate the switch 62 at a later time (eg, for another treatment on the same or a different patient). Actuation of the switch 62 reconnects the power circuit 120 by connecting the switch terminals 112, 114 and enables the coupled controller 52 and drug unit 70 to be ready for application to the patient and continuation of therapeutic agent delivery as before.

Figure 5:
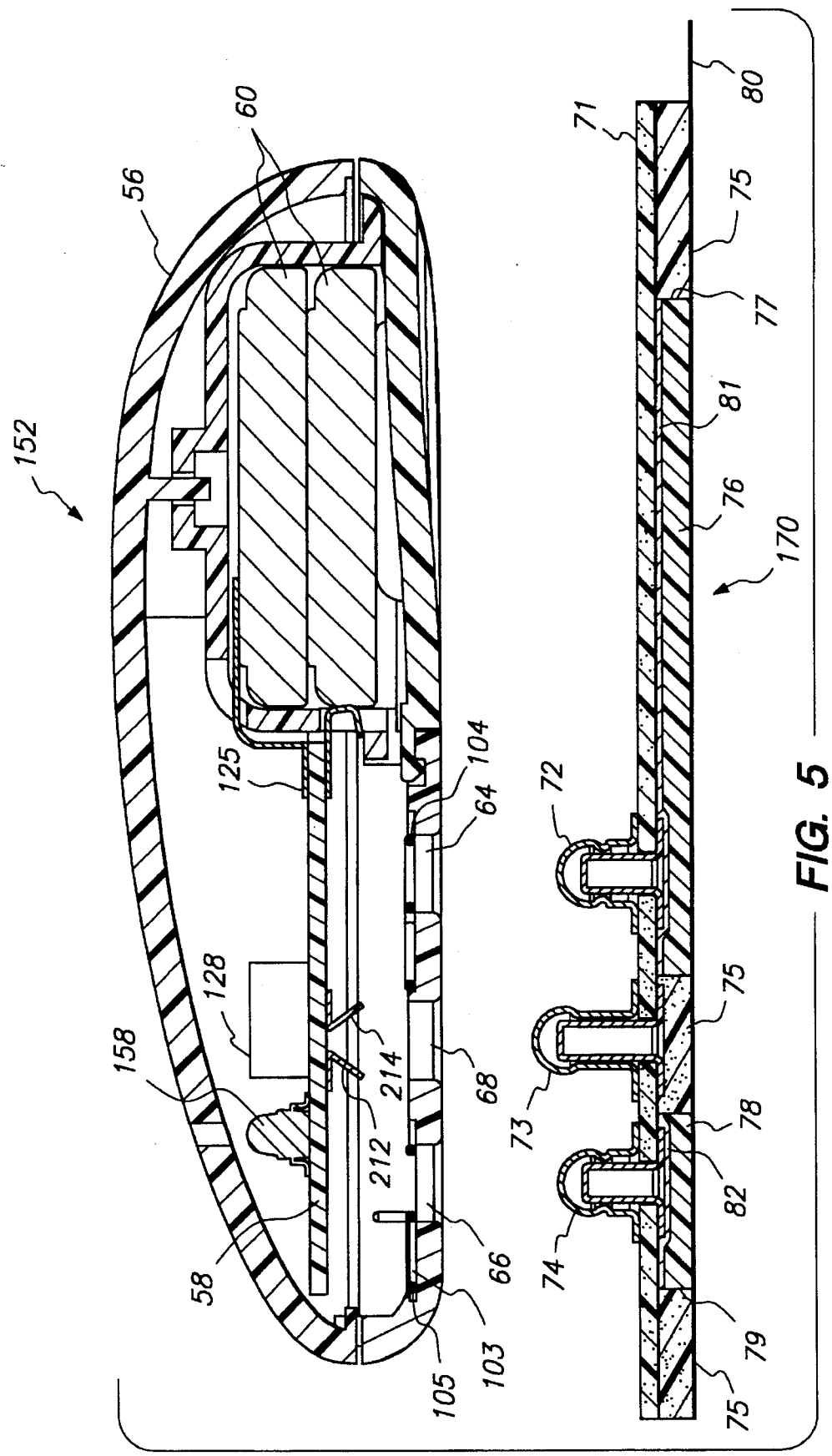
FIG. 5 is a cross sectional view of another electrotransport device with the controller and the drug unit in an uncoupled configuration, the drug unit having a third stud 73.
Figure 6:
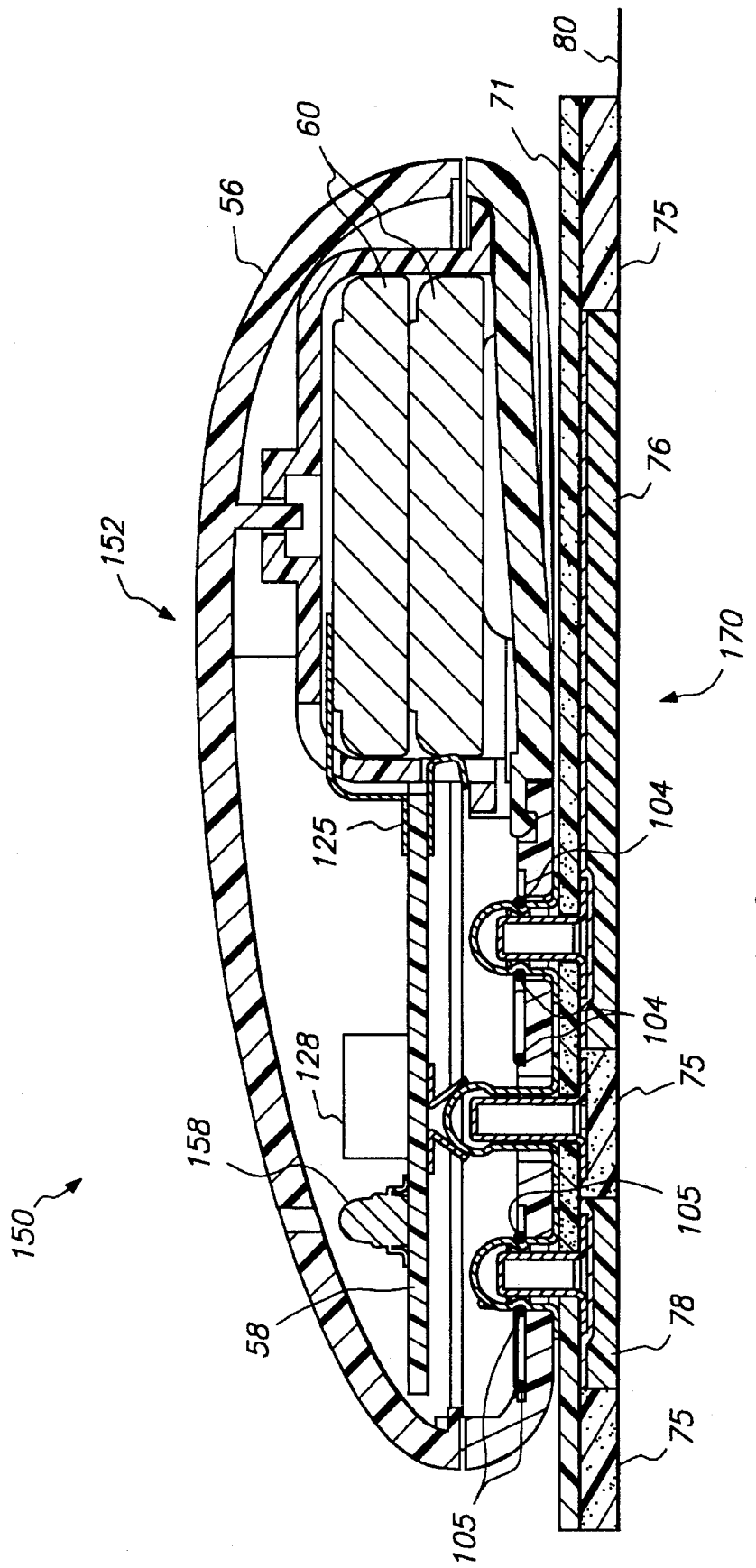
FIG. 6 is a cross sectional view of the device shown in FIG. 5 with the controller and the drug unit in a coupled configuration.

Referring now to FIGS. 5 and 6 there is shown an electrotransport device 150 comprised of a reusable electronic controller 152 and a disposable drug unit 170. Unlike device 50 illustrated in FIGS. 1–3, the reusable controller 152 has a third opening 68 adapted to receive a third stud 73 on drug unit 170. At least the head portion of stud 73 is composed of an electrically conductive material (eg, a metal or a metal coated polymer). The bottom of circuit board 58 in controller 152 includes a pair of spring terminals 212, 214 which are open and correspond in function to the terminals 112, 114 in controller 52. When drug unit 170 is coupled to controller 152, stud 73 extends through opening 68 and engages the spring terminals 212, 214. Because the head of stud 73 is electrically conductive, the engagement of stud 73 with a spring terminals 212, 214 closes the circuit between the terminals 212, 214 and thereby connects the power source 60 into the circuit 128.

Figure 7:
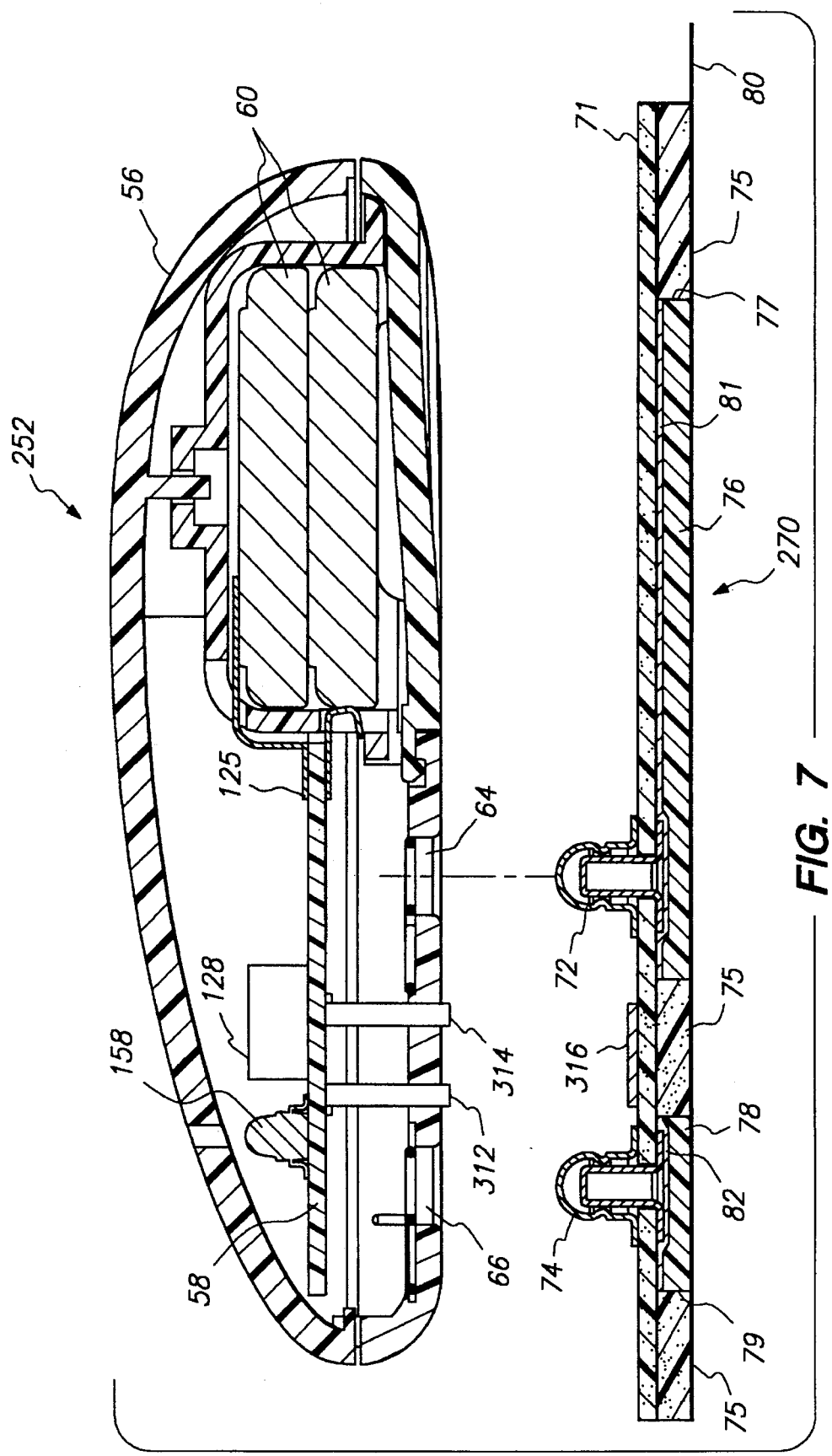
FIG. 7 is a cross sectional view of another electrotransport device with the controller and the drug unit in an uncoupled configuration, the controller having posts 312, 314 and the drug unit having a conductive strip 316.
Figure 8:
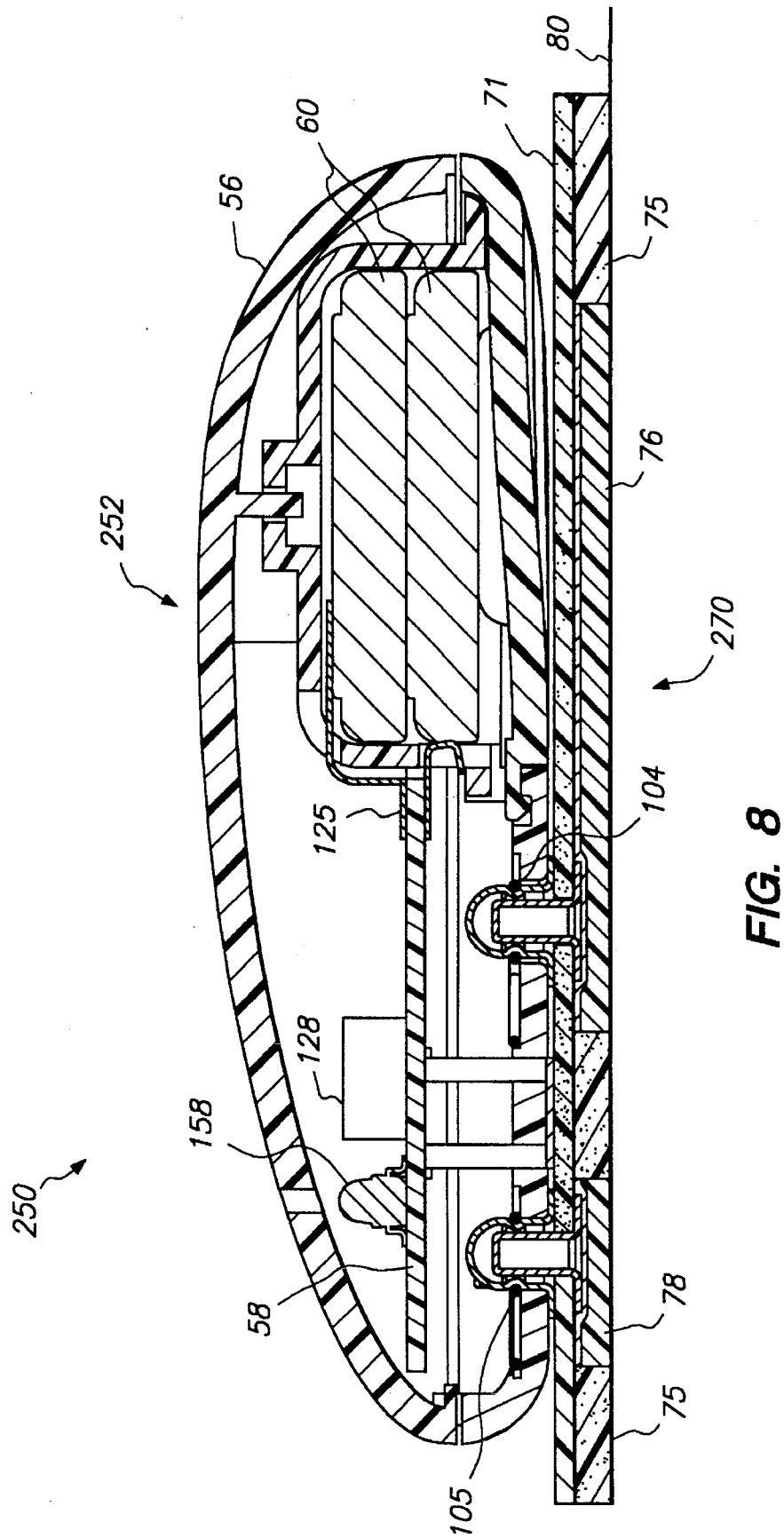
FIG. 8 is a cross sectional view of the device shown in FIG. 7 with the controller and the drug unit in a coupled configuration.

Referring now to FIGS. 7 and 8, an electrotransport device 250 comprised of a reusable electronic controller 252 and a disposable drug unit 270 is illustrated. Unlike device 50 shown in FIGS. 1–3, device 250 includes electrically conductive posts 312, 314 which extend through the bottom of housing 56. The ends of posts 312, 314 are adapted to contact conductive strip 316, which is carried on the upper surface of substrate 71, when the drug unit 270 is coupled to controller 252, as shown in FIG. 8. Electrically conductive post 312, 314 perform a similar function as the terminals 112, 114 in device 50. Thus, when the controller 252 is uncoupled from the drug unit 270, an open circuit exists between the posts 312, 314, thereby electrically isolating the power source 60 from the circuit carried by the circuit board 58. Upon coupling the drug unit 270 to the controller 252, the posts 312, 314 engage the electrically conductive strip 316, thereby closing the open circuit and connecting the power source 60 to the circuitry on circuit board 58.

Like device 50, illustrated in FIGS. 2 and 3, devices 150 and 250 have a mechanical switching means which isolates the power source 60 from an internal closed loop timing circuit 128 on circuit board 58. But for the mechanical switching means, the closed loop timing circuit 128 would otherwise draw small amounts of current, even without the drug units coupled to the controller. Thus, the mechanical switching means (ie, switch 62, stud 73 and spring terminals 212, 214; and posts 312, 314 in combination with conductive strip 316) prevents the closed internal circuit 128 from being electrically connected to the power source 60 until just before the device is to be used, ie, when the drug unit is coupled to the controller. Those skilled in the art will readily appreciate that other known mechanical switches which draw no quiescent current from the power source 60 could be substituted for the switches illustrated in FIGS. 2–3 and 5–8, without departing from the spirit of the present invention.

While the device 50 illustrated in FIGS. 2 and 3 has stud 72 which performs two functions, namely electrically connecting electrode assembly 81, 76 to the circuit on circuit board 58, stud 72 also acts to close switch 62 and thereby connect the power source 60 to the circuit on circuit board 58. However, this "dual functionality" is not required as is clearly shown in devices 150 and 250 in FIGS. 5–8.

While the foregoing detailed description has described one embodiment of the electrotransport system having a reusable power saving controller in accordance with this invention, it is to be understood that the above description is illustrative only and not limiting of the disclosed invention. It will be appreciated that it would be possible for one skilled in the art to modify the shape, dimensions and materials of the housing, the PC board, batteries, switch and conductive traces, the components mounted and interconnected thereon, the electrode assembly, materials and type and shape of connectors and retaining springs, or to include or exclude various elements within the scope and spirit of this invention. Thus the invention is to be limited only by the claims as set forth below.

I claim:

1. In an electrotransport system for delivering a therapeutic agent through a body surface of a patient, the system including an assembly having a pair of electrodes, at least one of the electrodes containing the therapeutic agent to be delivered, and a controller, including a bipolar electrical power source and a current control circuit in electrical contact with both poles of the power source through a closed circuit path other than through the patient body surface, for providing electric current to the electrodes, and a coupler for coupling and uncoupling the controller and the assembly, the improvement comprising:

a switch connected to the coupler, for electrically connecting the power source to the control circuit upon coupling the controller and the assembly and for electrically disconnecting the power source from the circuit upon uncoupling the controller and the assembly.

2. The electrotransport system of claim 1, wherein the coupler comprises an electrically conductive snap connector.

3. The electrotransport system of claim 1, wherein the coupler comprises a pair of electrically conductive snap connectors.

4. The electrotransport system of claim 1, wherein the bipolar power source comprises a battery.

5. The electrotransport system of claim 1, wherein the assembly is adapted to be discarded after a single use.

6. The electrotransport system of claim 1, wherein the controller is adapted to be coupled to a plurality of assemblies in succession.

7. The electrotransport system of claim 1, wherein the current control circuit comprises a timing circuit which controls how long current is provided to the electrodes.

8. The electrotransport system of claim 1, wherein the coupler engages the switch to close the switch when the controller and the assembly are coupled.

9. The electrotransport system of claim 1, wherein the switch is a biased single pole, single throw switch.

10. The electrotransport system of claim 1, wherein the switch comprises a stud which contacts a pair of spring terminals.

11. The electrotransport system of claim 1, wherein the switch comprises a pair of posts and an electrically conductive strip.

12. A method of operating an electrotransport system for delivering a therapeutic agent through a body surface of a patient, the system including an assembly having a pair of electrodes, at least one of the electrodes containing the therapeutic agent to be delivered, and a controller, including a bipolar electrical power source and a current control circuit in electrical contact with both poles of the power source through a closed circuit path other than through the body surface, for providing electric current to the electrodes, a coupler for coupling and uncoupling the controller and the electrode assembly, and a switch operatively connected to the coupler, comprising:

coupling the controller and the assembly, the coupling causing the switch to electrically connect the power source to the control circuit; and subsequently uncoupling the controller and the assembly, the uncoupling causing the switch to electrically disconnect the power source from the control circuit.

13. The method of claim 12, wherein the coupling of the controller and the assembly is achieved by means of an electrically conductive snap connector.

14. The method of claim 12, wherein the coupling of the controller and the assembly is achieved by means of a pair of electrically conductive snap connectors.

15. The method of claim 12, wherein the bipolar power source comprises a battery.

16. The method of claim 12, including discarding the assembly after the assembly is uncoupled from the controller.

17. The method of claim 12, including coupling the controller to a second identical assembly after the first assembly is uncoupled from the controller.

18. The method of claim 12, wherein the current control circuit controls how long current is provided to the electrodes.

19. The method of claim 12, wherein the coupler engages the switch to close the switch when the controller and the assembly are coupled.

20. The method of claim 12, including signalling when the switch electrically connects the power source to the control circuit.

* * * * *